(12) United States Patent
Hicks

(10) Patent No.: US 7,506,720 B1
(45) Date of Patent: Mar. 24, 2009

(54) ANIMAL EAR PROTECTION APPARATUS

(76) Inventor: Tammera D. Hicks, 213 S. Saint Marks Ave., Chattanooga, TN (US) 37411

( * ) Notice: Subject to any disclaimer, the term of this patent is extended or adjusted under 35 U.S.C. 154(b) by 80 days.

(21) Appl. No.: 11/490,271

(22) Filed: Jul. 21, 2006

(51) Int. Cl.
*A61B 7/02* (2006.01)

(52) U.S. Cl. .................. 181/135; 54/80.1; 54/80.4; 119/719; 119/850; 119/855; 128/864; 181/131; 381/313; 381/322; D24/106; D30/144

(58) Field of Classification Search ............ 181/135, 181/131; 381/313, 322; 128/864; D24/106; D30/144; 119/719, 850, 851, 855; 54/80.1, 54/80.2, 80.4
See application file for complete search history.

(56) References Cited

U.S. PATENT DOCUMENTS

| | | | | |
|---|---|---|---|---|
| 2,446,707 A | * | 8/1948 | Leight | 128/864 |
| 2,641,328 A | * | 6/1953 | Beaudry | 181/132 |
| 2,803,308 A | * | 8/1957 | Di Mattia | 181/135 |
| 2,876,767 A | * | 3/1959 | Wasserman | 128/865 |
| 2,888,921 A | * | 6/1959 | Nielson et al. | 128/865 |
| 3,047,089 A | * | 7/1962 | Zwislocki | 181/135 |
| 3,303,902 A | * | 2/1967 | Knott | 181/135 |
| 3,415,246 A | * | 12/1968 | Hill | 128/864 |
| 3,603,309 A | * | 9/1971 | Wesemann | 128/868 |
| 3,771,521 A | * | 11/1973 | Kittredge | 128/864 |
| 3,833,701 A | * | 9/1974 | Johnson et al. | 264/129 |
| 4,089,332 A | * | 5/1978 | Rose | 128/865 |
| 4,223,189 A | * | 9/1980 | Warren | 181/135 |
| 4,253,452 A | * | 3/1981 | Powers et al. | 128/864 |
| 4,338,929 A | * | 7/1982 | Lundin et al. | 128/864 |
| 4,582,053 A | * | 4/1986 | Wilson | 128/867 |
| 4,587,965 A | * | 5/1986 | de Boer et al. | 128/867 |
| 4,852,684 A | * | 8/1989 | Packard | 181/131 |
| 4,913,259 A | * | 4/1990 | Packard | 181/131 |
| 4,964,264 A | * | 10/1990 | Adams | 54/80.1 |
| 5,074,375 A | * | 12/1991 | Grozil | 181/135 |
| 5,080,110 A | * | 1/1992 | Weldon et al. | 128/864 |
| 5,188,123 A | * | 2/1993 | Gardner, Jr. | 128/864 |
| 5,288,953 A | * | 2/1994 | Peart | 181/130 |
| 5,333,622 A | * | 8/1994 | Casali et al. | 128/864 |
| 5,421,818 A | * | 6/1995 | Arenberg | 604/21 |
| 5,449,865 A | * | 9/1995 | Desnick et al. | 181/131 |
| D366,313 S | * | 1/1996 | Krause | D24/106 |
| 5,917,918 A | * | 6/1999 | Callahan | 381/67 |
| D413,379 S | * | 8/1999 | Leight | D24/106 |
| D417,315 S | * | 11/1999 | Lowry | D30/144 |
| 6,006,361 A | * | 12/1999 | Falco et al. | 2/209 |
| 6,241,042 B1 | * | 6/2001 | Falco | 181/135 |
| 6,256,396 B1 | * | 7/2001 | Cushman | 381/328 |
| 6,408,981 B1 | * | 6/2002 | Smith et al. | 181/126 |

(Continued)

FOREIGN PATENT DOCUMENTS

FR 2581505 A1 * 11/1986

*Primary Examiner*—Walter Benson
*Assistant Examiner*—Christina Russell

(57) ABSTRACT

An animal ear protection apparatus includes a substantially solid plug that is comprised of a resiliently compressible material. The plug has a first end, a second end and a peripheral surface extending between the first and second ends. The first end is substantially planar. The second end is convexly arcuate. The first end has a substantially annular perimeter edge. A grip is attached to the plug and extends away from the second end. The first end of the plug is insertable into an ear canal of a canine and retrievable therefrom with the grip.

6 Claims, 4 Drawing Sheets

U.S. PATENT DOCUMENTS

| | | | |
|---|---|---|---|
| D467,333 S * | 12/2002 | Martinson | D24/106 |
| D471,625 S * | 3/2003 | Falco | D24/106 |
| 6,591,786 B1 * | 7/2003 | Davis | 119/719 |
| 6,595,317 B1 * | 7/2003 | Widmer et al. | 181/135 |
| D478,658 S * | 8/2003 | Falco | D24/106 |
| 6,773,405 B2 * | 8/2004 | Fraden et al. | 600/549 |
| D496,722 S * | 9/2004 | Falco et al. | D24/106 |
| 7,331,310 B1 * | 2/2008 | Sersland et al. | 119/712 |
| 7,394,909 B1 * | 7/2008 | Widmer et al. | 381/322 |
| 2002/0080979 A1 * | 6/2002 | Brimhall et al. | 381/72 |
| 2003/0002703 A1 * | 1/2003 | Ma | 381/371 |
| 2003/0075185 A1 * | 4/2003 | Ulbrich | 128/864 |
| 2003/0112990 A1 * | 6/2003 | McIntosh et al. | 381/322 |
| 2003/0165248 A1 * | 9/2003 | Lenz et al. | 381/312 |
| 2003/0172938 A1 * | 9/2003 | Falco | 128/864 |
| 2004/0254497 A1 * | 12/2004 | Fraden et al. | 600/549 |
| 2005/0008180 A1 * | 1/2005 | Smith et al. | 381/328 |
| 2005/0274568 A1 * | 12/2005 | Falco et al. | 181/135 |
| 2006/0067551 A1 * | 3/2006 | Cartwright et al. | 381/322 |
| 2006/0081415 A1 * | 4/2006 | Knauer et al. | 181/135 |
| 2006/0177080 A1 * | 8/2006 | Smith | 381/313 |
| 2007/0062462 A1 * | 3/2007 | McGuire | 119/850 |
| 2007/0116309 A1 * | 5/2007 | Smith | 381/313 |
| 2007/0125590 A1 * | 6/2007 | Oberdanner | 181/135 |
| 2007/0183606 A1 * | 8/2007 | Doty | 381/72 |
| 2007/0183613 A1 * | 8/2007 | Juneau et al. | 381/322 |
| 2007/0284182 A1 * | 12/2007 | Mu | 181/135 |

\* cited by examiner

ANIMAL EAR PROTECTION APPARATUS

BACKGROUND OF THE INVENTION

1. Field of the Invention

The present invention relates to hearing protection devices and more particularly pertains to a new hearing protection device for protecting the eardrum of an animal, such as a horse or cat and in particular a canine, from loud sounds.

2. Description of the Prior Art

The use of hearing protection devices is known in the prior art. While these devices fulfill their respective, particular objectives and requirements, the need remains for a device that may be used for protecting the eardrum of domesticated animals. This is particularly important for such animals as canines that are used for hunting and therefore are subject to hearing guns being discharged.

SUMMARY OF THE INVENTION

The present invention meets the needs presented above by generally comprising a substantially solid plug that is comprised of a resiliently compressible material. The plug has a first end, a second end and a peripheral surface extending between the first and second ends. The first end is substantially planar. The second end is convexly arcuate. The first end has a substantially annular perimeter edge. A grip is attached to the plug and extends away from the second end. The first end of the plug is insertable into an ear canal of a canine and retrievable therefrom with the grip.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
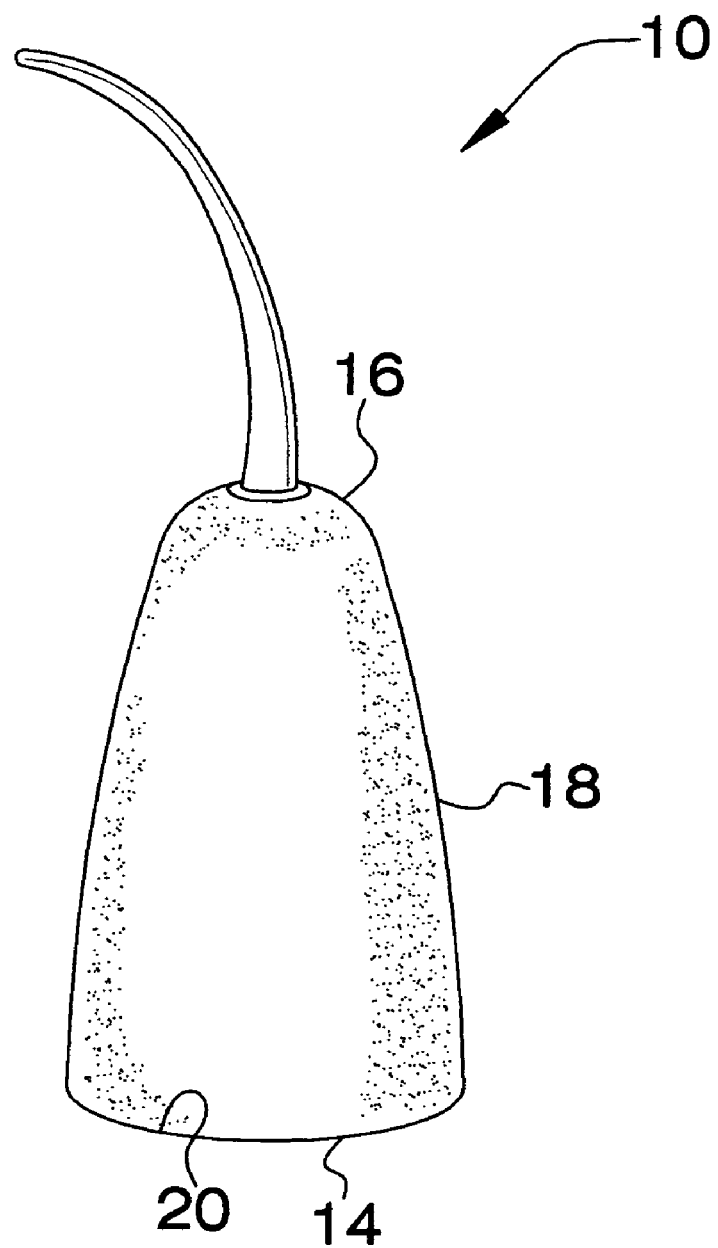
FIG. 1 is a side perspective view of an animal ear protection apparatus according to the present invention.
Figure 2:
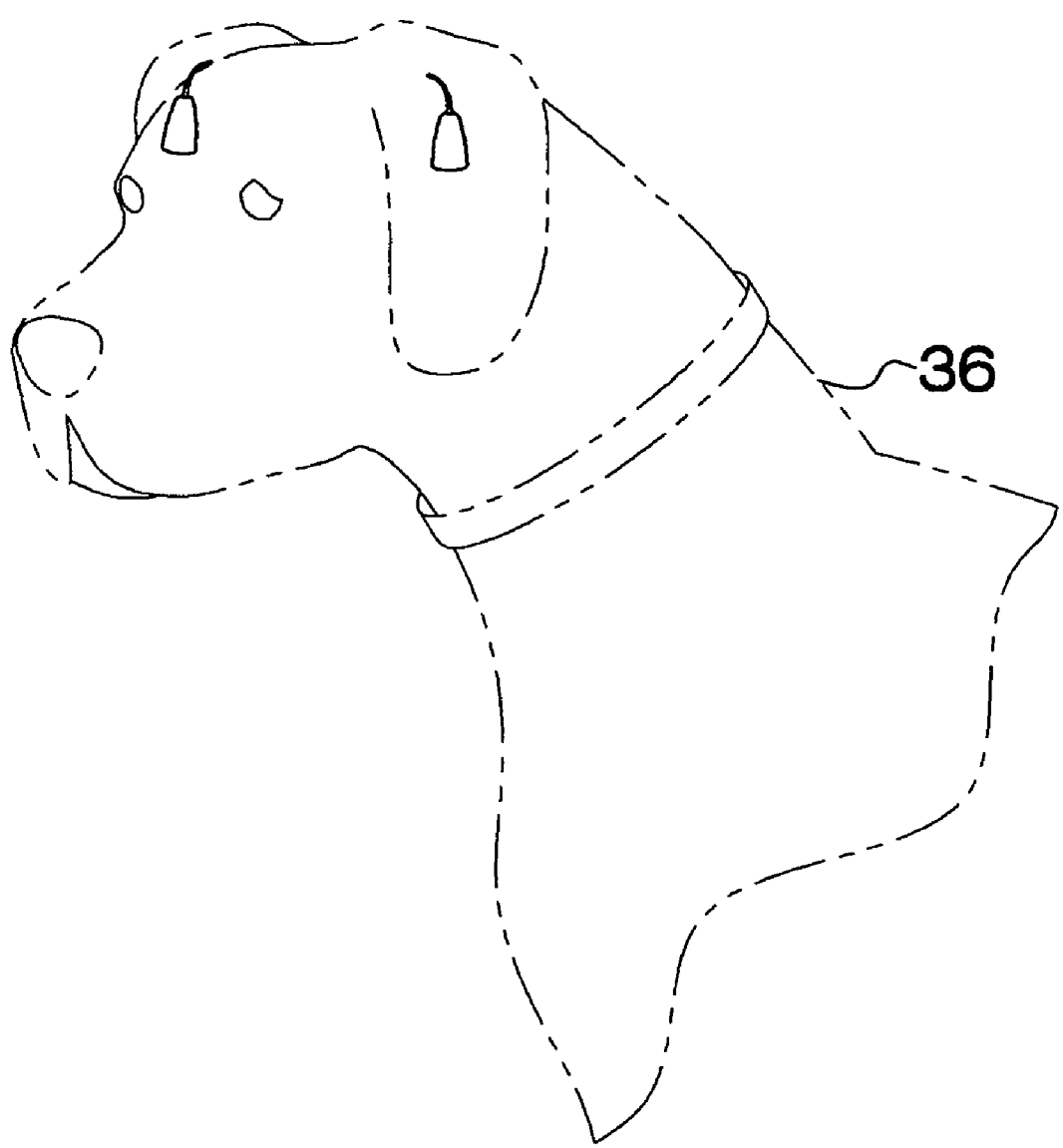
FIG. 2 is an in-use view of the present invention.
Figure 3:
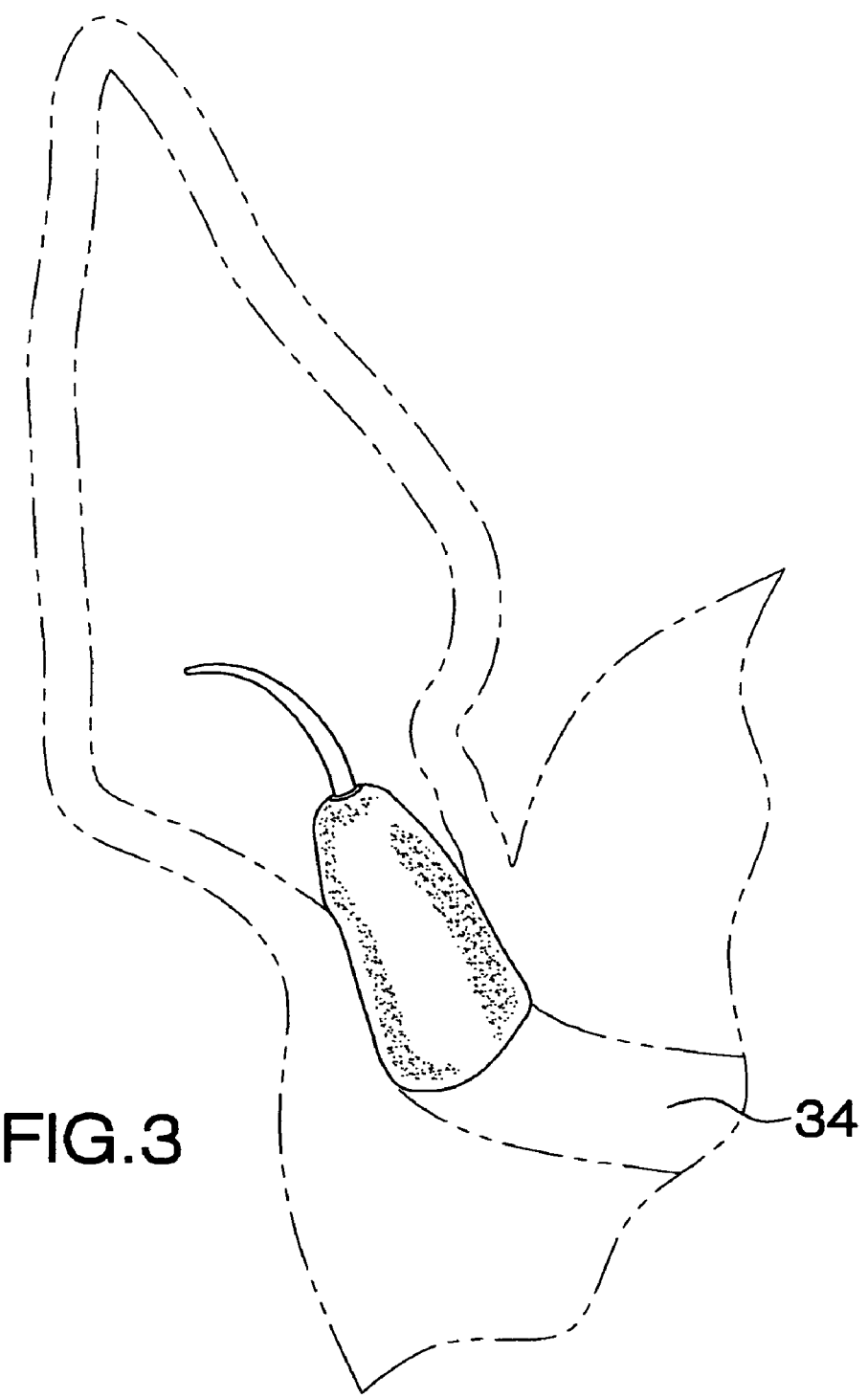
FIG. 3 is an in-use view of the present invention.
Figure 4:
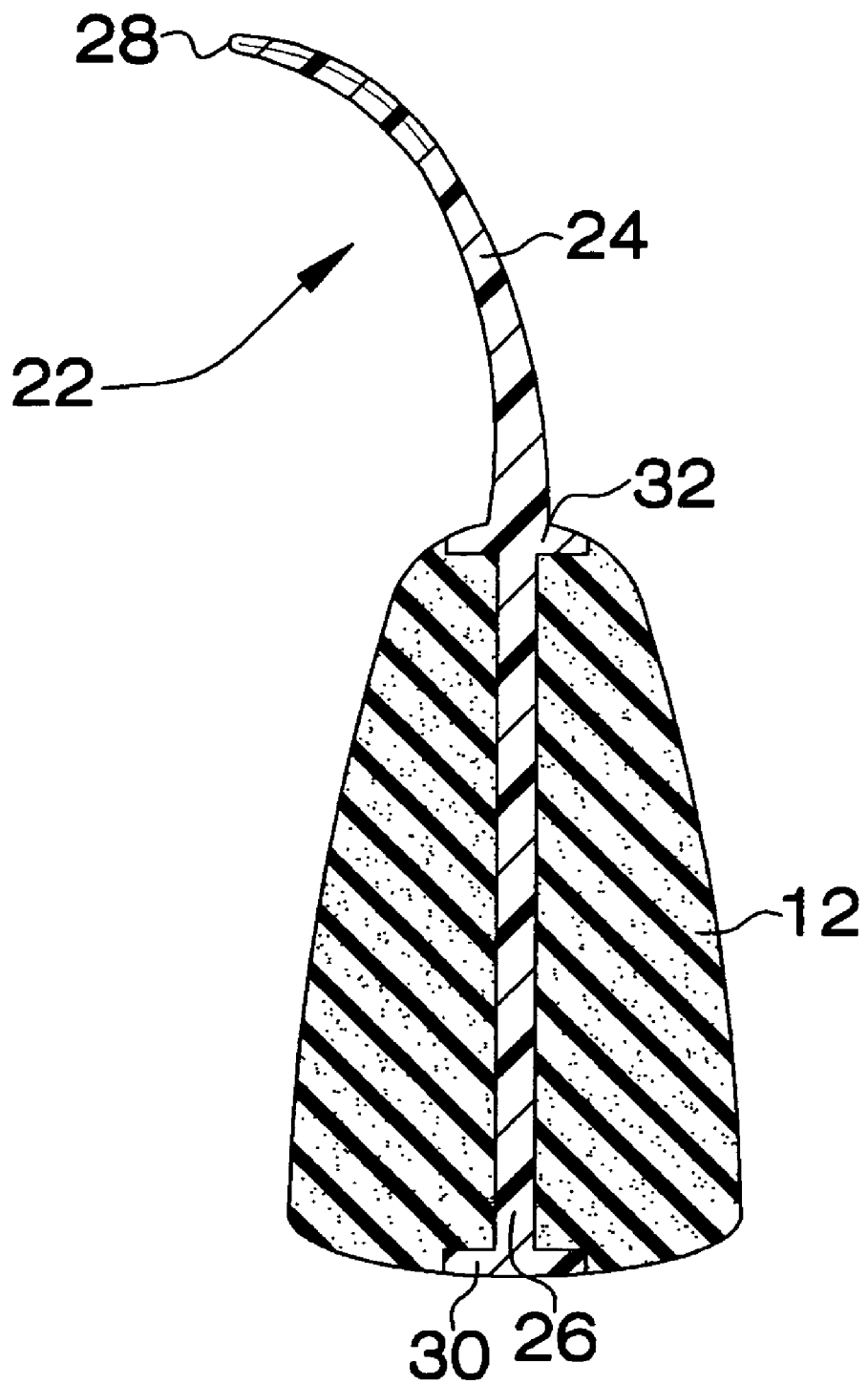
FIG. 4 is a side cross-sectional view of the present invention.

With reference now to the drawings, and in particular to FIGS. 1 through 4 thereof, a new hearing protection device embodying the principles and concepts of the present invention and generally designated by the reference numeral 10 will be described.

As best illustrated in FIGS. 1 through 4, the animal ear protection apparatus 10 generally comprises a substantially solid plug 12 that is comprised of a resiliently compressible material. The plug 12 has a first end 14, a second end 16 and a peripheral surface 18 extending between the first 14 and second 16 ends. The first end 14 is substantially planar and the second end 16 is convexly arcuate. The first end 14 has a substantially annular perimeter edge 20. A width of the plug 12 decreases from the first end 14 to the second end 16 and the plug 12 has a frusto-conical shape. The plug 12 has a height from the first end 14 to the second end 16 between about ¾ inch and 2 inches. The first end 14 has a width between about ¼ inch and 1 inch. The resiliently compressible material comprises a foamed elastomer.

A grip 22 is attached to the plug 12 and extends away from the second end 16. The grip 22 includes an elongated member 24 that has an attached end 26 and a free end 28. The attached end 26 is positioned in the plug 12. The free end 28 extends away from the second end 16 of the plug 12. A first stop 30 and a second stop 32 each is attached to and radially extend outwardly from a longitudinal axis of the elongated member 24. The first stop 30 is positioned adjacent to the first end 14 of the plug. The second stop 32 is positioned adjacent to the second end 16 of the plug 12. The first 30 and second 32 stops inhibit movement of the elongated member 24 relative to the plug.

In use, the first end 14 of the plug 12 is insertable into an ear canal 34 of a canine 36 or other animal and retrievable therefrom with the grip 22. While the plug 12 is positioned in the ear canal 34, it will prevent damage to the eardrum of the canine 36 during the emitting of any relatively loud sounds, like that from a gun.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A sound dampening apparatus for preventing injury to the hearing of a domesticated animal, said apparatus comprising:

a substantially solid plug being comprised of a resiliently compressible material, said plug having a first end, a second end and a peripheral surface extending between said first and second ends, said first end being substantially planar, said second end being convexly arcuate, said first end having a substantially annular perimeter edge;

a grip being attached to said plug and extending away from said second end, said grip including an elongated member having an attached end and a free end, said attached end being positioned in said plug, said free end extending away from said second end of said plug, said grip having a decreasing thickness from said plug to said free end; and wherein the first end of the plug is insertable into an ear canal of the animal and retrievable therefrom with said grip.

2. The apparatus according to claim 1, wherein a width of said plug decreases from said first end to said second end and said plug having a frusto-conical shape.

3. The apparatus according to claim 2, wherein said plug has a height from said first end to said second end between about ¾ inch and 2 inches and said first end has a width between about ¼ inch and 1 inch.

4. The apparatus according to claim 2, wherein said resiliently compressible material comprises a foamed elastomer.

5. The apparatus according to claim 1, wherein said grip further includes a first stop and a second stop each being attached to and radially extending outwardly from a longitudinal axis of said elongated member, said first stop being positioned adjacent to said first end of said plug, said second stop being positioned adjacent to said second end of said plug, said first and second stops inhibiting movement of said elongated member relative to said plug.

6. A sound dampening apparatus for preventing injury to the hearing of domesticated animal, said apparatus comprising:

a substantially solid plug being comprised of a resiliently compressible material, said plug having a first end, a second end and a peripheral surface extending between said first and second ends, said first end being substantially planar, said second end being convexly arcuate, said first end having a substantially annular perimeter edge, a width of said plug decreasing from said first end to said second end and said plug having a frusto-conical shape, said plug having a height from said first end to said second end between about ¾ inch and 2 inches, said first end having a width between about ¼ inch and 1 inch, said resiliently compressible material comprising a foamed elastomer;

a grip being attached to said plug and extending away from said second end, said grip including an elongated member having an attached end and a free end, said attached end being positioned in said plug, said free end extending away from said second end of said plug, a first stop and a second stop each being attached to and radially extending outwardly from a longitudinal axis of said elongated member, said first stop being positioned adjacent to said first end of said plug, said second stop being positioned adjacent to said second end of said plug, said first and second stops inhibiting movement of said elongated member relative to said plug, a thickness of said grip decreasing from said plug to said free end, said grip being arcuate from said plug to said free end; and wherein the first end of the plug is insertable into an ear canal of the animal and retrievable therefrom with said grip.

\* \* \* \* \*